United States Patent
Motofuji et al.

(10) Patent No.: US 11,299,587 B2
(45) Date of Patent: Apr. 12, 2022

(54) STARTING MATERIAL, FOR BULK DRUG OR ADDITIVES FOR DRUG, AND BULK DRUG OR DRUG USING SAME

(71) Applicant: SANYO CHEMICAL INDUSTRIES, LTD., Kyoto (JP)

(72) Inventors: Shihei Motofuji, Kyoto (JP); Kenichiro Nakai, Kyoto (JP); Kyosuke Michigami, Kyoto (JP); Itsuka Matsumoto, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 113 days.

(21) Appl. No.: 16/957,203

(22) PCT Filed: Dec. 21, 2018

(86) PCT No.: PCT/JP2018/047261
§ 371 (c)(1),
(2) Date: Jun. 23, 2020

(87) PCT Pub. No.: WO2019/131515
PCT Pub. Date: Jul. 4, 2019

(65) Prior Publication Data
US 2021/0363300 A1     Nov. 25, 2021

(30) Foreign Application Priority Data

Dec. 27, 2017   (JP) .............................. JP2017-250611

(51) Int. Cl.
*C08G 65/26*   (2006.01)
*C08G 65/333*   (2006.01)
*C08L 71/02*   (2006.01)

(52) U.S. Cl.
CPC .............. *C08G 65/33337* (2013.01); *C08G 65/2609* (2013.01); *C08L 71/02* (2013.01)

(58) Field of Classification Search
CPC ............ C08G 65/33337; C08G 65/332; C08G 65/3322; C08G 65/3328; C08G 65/333; C08G 65/2609; C08L 71/02; A61K 47/10
See application file for complete search history.

(56) References Cited

U.S. PATENT DOCUMENTS

| 2007/0031371 A1* | 2/2007 | McManus | A61K 31/74 |
| | | | 424/78.37 |
| 2010/0087672 A1 | 4/2010 | Khatri | |

(Continued)

FOREIGN PATENT DOCUMENTS

| EP | 1 373 366 | 1/2004 |
| EP | 2 518 098 | 10/2012 |

(Continued)

OTHER PUBLICATIONS

NOF Corporation, PEG Derivatives, Phospholipid and Drug Delivery Materials for Pharmaceuticals, 2003, p. 1-50.*
Song, X. et al., "Preparation of pH-sensitive amphiphilic block star polymers, their self-assembling characteristics and release behavior on encapsulated molecules" Polymer Bulletin, Jan. 2017, vol. 74., No. 1, pp. 183-194.
International Search Report dated Feb. 19, 2019 in corresponding International (PCT) Application No. PCT/JP2018/047261.
Sadao Mori, "High Performance Liquid Chromatography of Polymers", Size Exclusion Chromatography, Kyoritsu Publishing Co., Ltd., Dec. 10, 1991, with English translation.
Calculation of Mw/Mn of the Compound of Ex 8 of WO 2011/063156, Oct. 22, 2021.

*Primary Examiner* — Robert S Jones, Jr.
(74) *Attorney, Agent, or Firm* — Wenderoth, Lind & Ponack, L.L.P.

(57) ABSTRACT

The present invention provides a raw material for bulk drugs and a pharmaceutical additive which provide excellent formulation stability and excellent over-time stability of drug efficacy when used to modify a bulk drug, a polypeptide, a bioactive protein, an enzyme, and the like. The present invention relates to a raw material for bulk drugs or a pharmaceutical additive, containing: a polyether composition (A) represented by formula (1), wherein the polyether composition (A) has a unimodal molecular weight distribution, the polyether composition (A) has a ratio (Mw/Mn) of the weight average molecular weight (Mw) to the number average molecular weight (Mn) of 1.20 or less, and the polyether composition (A) contains a compound in which m is 1 in formula (1) in an amount of 90 wt % or more based on the weight of the polyether composition (A), in formula (1), $OR^1$, $R^2O$, $R^3O$, and $R^4O$ are each independently a C2-C8 oxyalkylene group; when each of these moieties exists in the plural number, each $OR^1$, each $R^2O$, each $R^3O$, and each $R^4O$ may be the same as or different from each other; these moieties may be bonded randomly or in block; a, b, c, and d are each independently an integer of 50 to 1200; $X^1$ to $X^4$ are each independently a hydrogen atom, a substituent represented by formula (2), or a substituent represented by formula (3); and m is an integer of 1 to 10.

[Chem. 1]

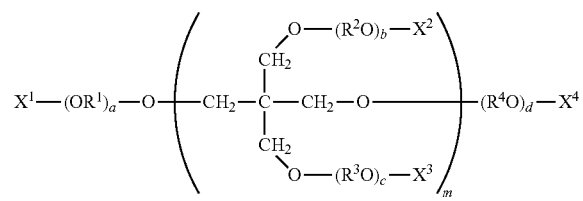

(1)

6 Claims, No Drawings

(56) References Cited

U.S. PATENT DOCUMENTS

| | | | |
|---|---|---|---|
| 2011/0200550 A1* | 8/2011 | Kozlowski | A61K 31/4745 424/78.17 |
| 2011/0286956 A1* | 11/2011 | Zhao | C08G 65/3344 424/78.3 |
| 2012/0282671 A1* | 11/2012 | Zhao | C08G 65/3322 435/188 |
| 2019/0016856 A1 | 1/2019 | Wei et al. | |

FOREIGN PATENT DOCUMENTS

| | | |
|---|---|---|
| JP | 2-149335 | 6/1990 |
| JP | 10-139878 | 5/1998 |
| JP | 2013-511539 | 4/2013 |
| JP | 2014-208794 | 11/2014 |
| WO | 2011/063156 | 5/2011 |
| WO | 2017/157188 | 9/2017 |

* cited by examiner

# STARTING MATERIAL, FOR BULK DRUG OR ADDITIVES FOR DRUG, AND BULK DRUG OR DRUG USING SAME

TECHNICAL FIELD

The present invention relates to a raw material for bulk drugs or a pharmaceutical additive, and a bulk drug or a pharmaceutical product including the same.

BACKGROUND ART

Conventionally, polyoxyalkylene compounds such as polyethylene glycol (macrogol) have been used for pharmaceutical products to serve as, for example, plasticizers, lubricants, stabilizers, solubilizers, bases, binders, suspending agents, brighteners, coating agents, wetting agents, wetting emulsifiers, sugar coating, adhesion enhancers, viscosity adjusters, excipients, dispersants, solvents, solubilization aids, disintegrants, anti-moisture agents, modifiers, and raw materials for drug delivery systems.

In particular, multibranched polyoxyalkylene derivatives have been proposed for modification of bulk drugs, polypeptides, bioactive proteins, enzymes, and the like, and for drug delivery systems such as liposomes and polymer micelles (for example, see Patent Literature 1).

CITATION LIST

Patent Literature

Patent Literature 1: JP H10-139878 A

Yet, when the multibranched polyoxyalkylene derivative disclosed in Patent Literature 1 is used to modify a bulk drug, a polypeptide, a bioactive protein, an enzyme, and the like, it results in insufficient formulation stability and insufficient over-time stability of drug efficacy.

SUMMARY OF INVENTION

Technical Problem

The present invention was made in view of the above problems, and aims to provide a raw material for bulk drugs or a pharmaceutical additive which provides excellent formulation stability and excellent over-time stability of drug efficacy when used to modify a bulk drug, a polypeptide, a bioactive protein, an enzyme, and the like.

Solution to Problem

As a result of extensive studies to achieve the above object, the present inventors arrived at the present invention. Specifically, the present invention provides a raw material for bulk drugs or a pharmaceutical additive, containing: a polyether composition (A) represented by formula (1), wherein the polyether composition (A) has a unimodal molecular weight distribution, the polyether composition (A) has a ratio (Mw/Mn) of the weight average molecular weight (Mw) to the number average molecular weight (Mn) of 1.20 or less, and the polyether composition (A) contains a compound in which m is 1 in formula (1) in an amount of 90 wt % or more based on the weight of the polyether composition (A),

[Chem. 1]

$$X^1-(OR^1)_n-O-\left[CH_2-\underset{\underset{\underset{O-(R^3O)_c-X^3}{|}}{\overset{\overset{O-(R^2O)_b-X^2}{|}}{CH_2}}}{C}-CH_2-O\right]_m-(R^4O)_d-X^4 \quad (1)$$

in formula (1), $OR^1$, $R^2O$, $R^3O$, and $R^4O$ are each independently a C2-C8 oxyalkylene group; when each of these moieties exists in the plural number, each $OR^1$, each $R^2O$, each $R^3O$, and each $R^4O$ may be the same as or different from each other; these moieties may be bonded randomly or in block; a, b, c, and d are each independently an integer of 50 to 1200; $X^1$ to $X^4$ are each independently a hydrogen atom, a substituent represented by formula (2), or a substituent represented by formula (3); and m is an integer of 1 to 10,

[Chem. 2]

$$-R^6-\underset{\underset{O}{\|}}{C}-OR^7 \quad (2)$$

[Chem. 3]

$$-R^6-\underset{\underset{O}{\|}}{C}-O-N\diagup\diagdown \quad (3)$$

in formulas (2) and (3), $R^6$ is a C1-C10 alkylene group; in formula (2), $R^7$ is a hydrogen atom or a C1-C15 monovalent hydrocarbon group in which a hydrogen atom may be replaced by a C1-C10 alkoxy group; and when a substituent represented by formula (2) or (3) exists in the plural number in formula (1), each $R^6$ and each $R^7$ in these substituents may be the same as or different from each other.

Advantageous Effects of Invention

The raw material for bulk drugs and the pharmaceutical additive of the present invention provide excellent formulation stability and excellent over-time stability of drug efficacy when used to modify a bulk drug, a polypeptide, a bioactive protein, an enzyme, and the like. A bulk drug or a pharmaceutical product containing the raw material for bulk drugs or the pharmaceutical additive of the present invention has excellent formulation stability and over-time stability of drug efficacy.

DESCRIPTION OF EMBODIMENTS

The raw material for bulk drugs and the pharmaceutical additive of the present invention contain a polyether composition (A) represented by formula (1).

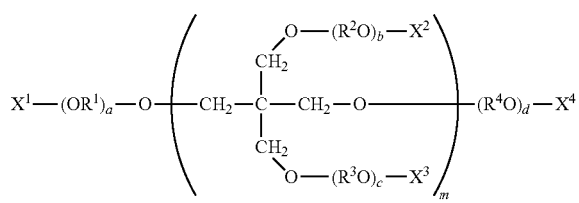

(1)

In formula (1), $OR^1$, $R^2O$, $R^3O$, and $R^4O$ are each independently a C2-C8 oxyalkylene group; when each of these moieties exists in the plural number, each $OR^1$, each $R^2O$, each $R^3O$, and each $R^4O$ may be the same as or different from each other.

Examples of the C2-C8 oxyalkylene group include an oxyethylene group, a 1,2- or 1,3-oxypropylene group, a 1,2-, 1,3-, 1,4-, or 2,3-oxybutylene group, an oxypentylene group, an oxyhexylene group, and an oxyoctylene group.

The C2-C8 oxyalkylene group is preferably one oxyethylene group used alone or a combination of an oxyethylene group and another oxyalkylene group, more preferably one oxyethylene group used alone or a combination of an oxyethylene group and an oxypropylene group, particularly preferably one oxyethylene group used alone, in view of formulation stability and over-time stability of drug efficacy after modification of a bulk drug, a polypeptide, a bioactive protein, an enzyme, and the like.

When an oxyethylene group and another oxyalkylene group are used in combination, preferably the amount of the oxyethylene group is 85 mol % or more based on the total number of moles of the oxyethylene group and the other oxyalkylene group(s).

When the oxyalkylene group is composed of two or more oxyalkylene groups, the polyoxyalkylene groups may be bonded randomly or in block. Yet, a block copolymer is preferred in view of formulation stability and over-time stability of drug efficacy after modification of a bulk drug, a polypeptide, a bioactive protein, an enzyme, and the like.

In formula (1), a, b, c, and d are each independently an integer of 50 to 1200.

When each integer is less than 50 or more than 1200, it results in poor formulation stability and poor over-time stability of drug efficacy after modification of a bulk drug, a polypeptide, a bioactive protein, an enzyme, and the like.

In addition, each of a, b, c, and d is preferably 50 to 1100, more preferably 50 to 700, in view of formulation stability and over-time stability of drug efficacy after modification of a bulk drug, a polypeptide, a bioactive protein, an enzyme, and the like.

When the oxyalkylene groups are bonded in block (including a case where one oxyalkylene group is used alone), each of a, b, c, and d is preferably 50 to 1100, more preferably 50 to 1000, particularly preferably 50 to 700, in order to further improve formulation stability and over-time stability of drug efficacy after medication of a bulk drug, a polypeptide, a bioactive protein, an enzyme, and the like.

When the oxyalkylene groups are bonded randomly, each of a, b, c, and d is preferably 50 to 1100, more preferably 50 to 1000, particularly preferably 50 to 650, in order to further improve formulation stability and over-time stability of drug efficacy after modification of a bulk drug, a polypeptide, a bioactive protein, an enzyme, and the like.

Whether the oxyalkylene groups are bonded randomly or in block can be determined by assigning a signal from a dimer or a signal from a trimer by pyrolysis-gas chromatography.

The block form shows a characteristic signal different from that of the random from. For example, in diblock form of two components, i.e., a monomer A and a monomer B, the proportion of a signal from AA and the proportion of a signal from BB among signals from dimers are higher than those in random form, and the proportion of a signal from AB is lower than that in random form.

In addition, among signals from trimers, the proportion of a signal from AAA and the proportion of a signal from BBB are higher than those in random form, and the proportions of signals from other trimers (such as ABB) are lower than those in random form.

In addition to the measurement method by pyrolysis-gas chromatograph, the proportions of the above signals in random form can also be derived by calculating the ratio of each monomer constituting a random copolymer by $^1$H-NMR and using the Monte Carlo simulation method.

Measurement by pyrolysis-gas chromatography and measurement by $^1$H-NMR can be performed under the following conditions, for example.

<Example of Measurement Conditions for Pyrolysis-Gas Chromatography>
Curie point pyrolyzer: JHP-3 model (Japan Analytical Industry Co., Ltd.)
Gas chromatograph: HP-5890A (Hewlett Packard)
Mass spectrometer: JMS-DX303 (JEOL Ltd.)
Pyrolysis temperature: 445° C.
<Example of Measurement Conditions for $^1$H-NMR>
Solvent: deuterated methanol
Device: AVANCE300 (Bruker Japan K. K.)
Frequency: 300 MHz $X^1$ to $X^4$ in formula (1) are each independently a hydrogen atom, a substituent represented by formula (2), or a substituent represented by formula (3).

[Chem. 5]

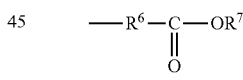

(2)

[Chem. 6]

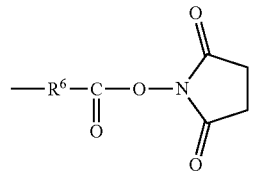

(3)

$R^6$ in formulas (2) and (3) is a C1-C10 alkylene group. When a substituent represented by formula (2) or (3) exists in the plural number in formula (1), each $R^6$ and each $R^7$ in these substituents may be the same as or different from each other.

Examples of the C1-C10 alkylene group include methylene, ethylene, 1,3-propylene, 1-methylethylene, 1,4-butylene, 1-ethylethylene, 1-methylpropylene, 2-methylpropylene, 1,5-pentyl, 1-methylbutylene, 2-methylbutylene, 1,1-dimethylpropylene, 1,2-dimethylpropylene, 1-ethylpropylene, 2-ethylpropylene, 1,6-hexylene, 1,4-cyclohexylene, 1,8-octylene, 2-ethyloctylene, 1,9-nonylene, and 1,10-decylene groups.

Of these, the C1-C10 alkylene group is preferably a C1-C10 straight-chain alkylene group, more preferably an ethylene group, a 1,3-propylene group, a 1,5-pentylene group, or a 1,6-hexylene group, in view of formulation stability and over-time stability of drug efficacy after modification of a bulk drug, a polypeptide, a bioactive protein, an enzyme, and the like.

$R^7$ in formula (2) is a hydrogen atom or a C1-C15 monovalent hydrocarbon group in which a hydrogen atom may be replaced by a C1-C10 alkoxy group. When a substituent represented by formula (2) exists in the plural number in formula (1), each $R^7$ in these substituents may be the same as or different from each other.

Examples of the C1-C10 alkoxy group include methoxy, ethoxy, propoxy, butoxy, and decoxy groups.

Examples of the C1-C15 monovalent hydrocarbon group include C1-C15 acyclic hydrocarbon groups (e.g., methyl, ethyl, iso-propyl, tert-butyl, and neopentyl groups), C3-C15 alicyclic hydrocarbon groups (e.g., cyclohexyl and adamantly groups), and C1-C15 aromatic hydrocarbon groups (e.g., phenyl, benzyl, p-methylbenzyl, and phenethyl groups).

Of these, the C1-C15 monovalent hydrocarbon group is preferably a C1-C15 acyclic hydrocarbon group, more preferably a tert-butyl group. When the C1-C15 monovalent hydrocarbon group is one of the above preferred groups, it results in an efficient synthesis reaction to synthesize a polyether composition represented by formula (1) in which $X^1$ to $X^4$ are substituents represented by formula (3), using a polyether composition represented by formula (1) in which $X^1$ to $X^4$ are substituents represented by formula (2) (described in detail later).

When the polyether composition (A) is used as a raw material for bulk drugs, preferably, $X^1$ to $X^4$ are substituents represented by formula (3), in view of formulation stability and over-time stability of drug efficacy after modification of a bulk drug, a polypeptide, a bioactive protein, an enzyme, and the like. When the polyether composition (A) is used as an additive for pharmaceutical products, $X^1$ to $X^4$ are preferably substituents represented by formula (2), in view of formulation stability and over-time stability of drug efficacy.

In formula (1), m is an integer of 1 to 10.

In view of formulation stability and over-time stability of drug efficacy after modification of a bulk drug, a polypeptide, a bioactive protein, an enzyme, and the like, the polyether composition (A) contains a compound in which m=1 in an amount of 90 wt % or more, preferably 92 wt % or more, more preferably 94 wt % or more, particularly preferably 95 wt % or more, more particularly preferably 98 wt % or more, most preferably 99 wt % or more, based on the weight of the polyether composition (A).

It is particularly preferred when the polyether composition (A) contains a compound in which m=1 in an amount of 95 wt % or more, because haze can be reduced when the polyether composition (A) is dissolved in a saline solution.

In order to further improve formulation stability and over-time stability of drug efficacy after modification of a bulk drug, a polypeptide, a bioactive protein, an enzyme, and the like, the polyether composition (A) is a composition containing a compound in which m is 1 to 10 and contains a compound in which m=1 in an amount of 90 wt % or more. Preferably, the polyether composition (A) is a composition containing a compound in which m is 1 to 8 and contains a compound in which m=1 in an amount of 92 wt % or more.

More preferably, the polyether composition (A) is a composition containing a compound in which m is 1 to 7 and contains a compound in which m=1 in an amount of 94 wt % or more. Particularly preferably, the polyether composition (A) is a composition containing a compound in which m is 1 to 7 and contains a compound in which m=1 in an amount of 95 wt % or more. More particularly preferably, the polyether composition (A) is a composition containing a compound in which m is 1 to 7 and contains a compound in which m=1 in an amount of 98 wt % or more. Most preferably, the polyether composition (A) is a composition containing a compound in which m is 1 to 7 and contains a compound in which m=1 in an amount of 99 wt % or more.

The amount of a compound in which m=1 can be determined by calculation from the amount of starting materials (e.g., pentaerythritol) and the amount of alkylene oxide (e.g., ethylene oxide) used in the later-described method of producing the polyether composition (A).

The amount of a compound in which m=1 can be adjusted to the above preferred ranges by subjecting starting materials (such as pentaerythritol) used in the later-described method of producing the polyether composition (A) to purification by column chromatography or the like before reaction so as to remove dipentaerythritol and the like.

The number average molecular weight (hereinafter abbreviated as Mn) of the polyether composition (A) represented by formula (1) is preferably 10000 to 200000, more preferably 10000 to 180000, particularly preferably 10000 to 130000, in view of formulation stability and over-time stability of drug efficacy after modification of a bioactive protein, an enzyme, and the like.

It is essential that the molecular weight distribution of the polyether composition (A) represented by formula (1) is unimodal, in view of formulation stability and over-time stability of drug efficacy after modification of a bioactive protein, an enzyme, and the like.

The term "unimodal" as used herein refers to a case where a compound represented by formula (1) has a single maximum peak in a graph when measured by gel permeation chromatography under the later-described conditions, wherein the graph shows the elution time of the elution peak of the compound represented by formula (1) on the horizontal axis, and the differential refractive index (RI) on the vertical axis, and the differential refractive index (RI) per elution time is plotted. A peak having an area of 3.5% or more relative to the total peak area is defined as the peak.

In order to provide a unimodal molecular weight distribution, preferably, the purity of starting materials (e.g., pentaerythritol) of the polyether composition (A) in the later-described method of producing the polyether composition (A) is increased, or an alkylene oxide (e.g., ethylene oxide) is ring-opening polymerized with a starting material (e.g., pentaerythritol) in the presence of the polyether composition (A) as a dispersant which weighs 0.05 to 5 times more than the starting material.

In addition, the ratio (Mw/Mn) of the weight average molecular weight (herein abbreviated as Mw) to Mn of the polyether composition (A) is preferably 1.20 or less, more preferably 1.15 or less, particularly preferably 1.10 or less, in view of formulation stability and over-time stability of drug efficacy after modification of a bioactive protein, an enzyme, and the like.

In order to provide a Mw/Mn of 1.20 or less, during ring-opening polymerization of an alkylene oxide (e.g., ethylene oxide) with a starting material (e.g., pentaerythritol), the oxygen concentration of the gas phase is preferably 0.1% or less, the water content in each raw material is preferably 0.4 wt % or less, the reaction temperature is preferably 125° C. to 135° C., and the aging temperature is preferably 145° C. to 155° C.

In the present invention, Mn, Mw, and molecular weight distribution of the polyether composition (A) can be determined by measurement by gel permeation chromatography (hereinafter abbreviated as GPC) under the following conditions, for example, and by calculation from the obtained molecular weight distribution curve, using a calibration curve of a standard substance such as standard polyethylene glycol.

<Example of Measurement Conditions for GPC>
Device: HLC-8320GPC available from Tosoh Corporation
Column: TSK gel Super AW available from Tosoh Corporation
Sample solution: 0.25 wt % solution in N,N-dimethylformamide (DMF)
Amount of solution to be injected: 10 μL
Flow rate: 0.6 mL/min
Measurement temperature: 40° C.
Mobile phase: DMF
Detector: refractive index detector In the raw material for bulk drugs or the pharmaceutical additive of the present invention, preferably, the amount of the polyether composition (A) is 0.1 to 99.5 wt % based on the weight of the raw material for bulk drugs or the pharmaceutical additive.

In the later-described method of producing a raw material for bulk drugs or a pharmaceutical additive, preferably, the polyether composition (A) is used in an amount that provides the above ratio. One polyether composition (A) of the present invention may be used alone or two or more thereof may be used in combination.

The method of producing the polyether composition (A) represented by formula (1) of the present invention is not limited. Examples include the following methods.

For example, in the presence of an alkaline catalyst such as potassium hydroxide, an alkylene oxide such as ethylene oxide is dropped at one time or sequentially into starting materials (e.g., pentaerythritol) under a reduced pressure at 100° C. to 200° C., followed by a further reaction at 100° C. to 200° C. for 0.5 to 10 hours. After optionally removing unreacted ethylene oxide under a reduced pressure, the catalyst is adsorbed or neutralized with phosphoric acid, and the solids are removed by filtration, thus obtaining a polyether composition represented by formula (1) in which $X^1$ to $X^4$ are hydrogen atoms.

In addition, for example, a polyether composition represented by formula (1) in which $X^1$ to $X^4$ are hydrogen atoms is dissolved in organic solvents (e.g., tetrahydrofuran and toluene), and a halide (a compound in which a halogen atom is bonded to a carboxy group via $R^6$: e.g., chloroacetic acid) is dropped into the solution at 25° C. to 40° C. in the presence of catalysts (e.g., potassium t-butoxide and sodium t-butoxide), followed by a further reaction at 25° C. to 40° C. for 1 to 24 hours. A by-product is removed by liquid separation, followed by recrystallization with an organic solvent such as isopropanol. Thus a polyether composition represented by in formula (1) in which $X^1$ to $X^4$ are substituents represented by formula (2) ($R^7$: hydrogen atom) can be obtained.

In addition, a polyether composition in which $X^1$ to $X^4$ in formula (1) are substituents represented by formula (2) ($R^7$: a C1-C15 monovalent hydrocarbon group in which a hydrogen atom may be replaced by a C1-C10 alkoxy group) can be produced by, for example, esterification by a known method between a carboxy group of a polyether composition represented by formula (1) in which $X^1$ to $X^4$ are substituents represented by formula (2) ($R^7$: hydrogen atom) and an alcohol in which a hydroxy group is bonded to a C1-C15 monovalent hydrocarbon group in which a hydrogen atom may be replaced by an C1-C10 alkoxy group.

Further, for example, a polyether composition represented by formula (1) in which $X^1$ to $X^4$ are substituents represented by formula (2) is dissolved in an organic solvent (e.g., N,N-dimethylformamide), and condensation agents (e.g., dicyclohexylcarbodiimide and 1-ethyl-3-(3-dimethylaminopropyl)carbodiimide hydrochloride) and N-hydroxysuccinimide are added to the solution, followed by a reaction at 25° C. to 40° C. for 1 to 24 hours. A by-product is removed by filtration, followed by recrystallization with an organic solvent such as isopropanol. Thus a polyether composition represented by formula (1) in which $X^1$ to $X^4$ are substituents represented by formula (3) can be obtained.

In formula (2), when $R^7$ is a hydrogen atom, esterification occurs between a carboxy group in formula (2) and a hydroxy group of N-hydroxysuccinimide. In addition, in formula (2), when $R^7$ is a C1-C15 monovalent hydrocarbon group in which a hydrogen atom may be replaced by a C1-C10 alkoxy group, an ester group in formula (2) undergoes transesterification.

Further, for example, a polyether composition represented by formula (1) in which $X^1$ to $X^4$ are substituents represented by formula (3) is dissolved in an organic solvent (e.g., N,N-dimethylformamide), and a known active ingredient (an active ingredient having a nucleophilic group (e.g. amino group) such as memantine hydrochloride) and optionally a base (e.g., triethylamine) are added to the solution, followed by a reaction at 100° C. for 1 to 18 hours. A by-product is removed by filtration, followed by recrystallization with organic solvents such as isopropanol and ethanol/methyl-t-butyl ether. Thus, a bulk drug modified with the raw material for bulk drugs of the present invention can be obtained.

The raw material for bulk drugs or the pharmaceutical additive of the present invention may contain known active ingredients that are used according to formulation properties and usage; other additives (e.g., excipients, binders, (solid) dispersants, thickeners, nucleating agents, solubilizers, sustained release agents, disintegrants, plasticizers, coating agents, bases, lubricants, stabilizers, preservatives, taste masking agents, odor masking agents, emulsifiers, antioxidants, pH adjusters, flavoring agents, and colorants) that are optionally used with these active ingredients; and water, for example.

Examples of the known active ingredients include ingredients described in Japanese Pharmacopoeia. Specific examples include digestive enzymes (e.g., protease, amylase, lipase, trypsin, chymotrypsin, carboxypeptidase, and ribonuclease), tamsulosin hydrochloride, ascorbic acid, aspirin, acetaminophen, ethyl aminobenzoate, benzoic acid, antipyrine, iopanoic acid, isosorbide, isopropylantipyrine, ibuprofen, indometacin, ethenzamide, ethacrynic acid, quinine ethyl carbonate, ethosuximide, testosterone enanthate, methenolone enanthate, epirizole, ergocalciferol, benzalkonium chloride, benzethonium chloride, acebutolol hydrochloride, alprenolol hydrochloride, amantadine hydrochloride, indenolol hydrochloride, L-ethylcysteine hydrochloride, ethylmorphine hydrochloride, etilefrine hydrochloride, oxprenolol hydrochloride, croconazole hydrochloride, cyclopentolate hydrochloride, dibucaine hydrochloride, tetracaine hydrochloride, trimetoquinol hydrochloride, phenylephrine hydrochloride, verapamil hydrochloride, meclofenoxate hydrochloride, oxethazaine, captopril, chlorphenesin carbamate, carmofur, xylitol, guaifenesin, clomiphene citrate, pentoxyverine citrate, diethylcarbamazine citrate, clinofibrate, clotiazepam, clotrimazole, chlorpropamide, ketoprofen, cholecalciferol, methenolone acetate, salicylic acid, diazepam, cyanamide, cyclophosphamide, disulfiram, diphenhydramine, cimetidine, dimenhydrinate, dextromethorphan hydrobromide, pyridostigmine bromide, scopolamine butylbromide, ifenprodil tartrate, simfibrate, thiamazole, thiotepa, tinidazole, trapidil, trimethadione, tolnaftate, tolbutamide, trepibutone, tropicamide, droperidol, nadolol, nicotinamide, bisacodyl, haloperidol, bifonazole, phenacetin, phenylbutazone, busulfan, formoterol fumarate, prazepam, fludiazepam, flurazepam, flurbiprofen, proglumide, progesterone, prothionamide, testosterone propionate, drostanolone propionate, perphenazine, benzbromarone, chlorpheniramine maleate, d-chlorpheniramine maleate, migrenin, miconazole, mequitazine, gabexate mesilate, deferoxamine mesylate, betahistine mesilate, mestranol, medazepam, metyrapone, neostigmine methylsulfate, methoxsalen, metoclopramide, menatetrenone, mefruside, ubidecarenone, echothiophate iodide, iodoform, riboflavin butyrate, lidocaine, 1-menthol, amphotericin B, alprostadil alfadex, epinephrine, cefcapene pivoxil hydrochloride, hydroxocobalamin acetate, retinol acetate, ergotamine tartrate, isosorbide nitrate (isosorbide mononitrate and isosorbide dinitrate), ceftibuten, trimethadione, nystatin, nitroglycerin, vasopressin, pantethine, bromocriptine mesylate, irinotecan, gemcitabine, mepitiostane, and memantine hydrochloride.

One of the above known active ingredients may be used alone, or two or more of them may be used in combination.

Examples of the other additives include the following compounds.

(1) Excipients: crystalline cellulose, ethyl cellulose, low-substituted hydroxypropyl cellulose, crosslinked polyvinylpyrrolidone, and the like
(2) Binders: hydroxypropyl cellulose, polyvinylpyrrolidone, polyvinyl alcohol, and the like
(3) (Solid) dispersants: hydroxypropyl methyl cellulose acetate succinate and the like
(4) Thickeners: methyl cellulose, sodium carboxymethyl cellulose, and the like
(5) Nucleating agents: lactose and the like
(6) Solubilizers: polyethylene glycol, propylene glycol, glycerol, α-cyclodextrin, polyoxyethylene (degree of polymerization: 20) sorbitan monooleate (Polysorbate 80), and the like
(7) Sustained release agents: ethyl cellulose, cellulose acetate, copolymers of vinyl acetate and vinyl chloride, hydroxypropyl methyl cellulose, sodium carboxymethyl cellulose, stearyl alcohol, and the like.
(8) Disintegrants: carmellose, carboxymethyl ethyl cellulose, low-substituted hydroxypropyl cellulose, crosslinked polyvinylpyrrolidone, hydroxypropyl starch, and the like
(9) Plasticizers: polyethylene glycol (degree of polymerization: 2 to 400), polyoxyethylene (degree of polymerization: 20) sorbitan monooleate (Polysorbate 80), olive oil, glycerol, sorbitol, sucrose, and the like
(10) Coating agents: hydroxypropyl methyl cellulose, ethyl cellulose, polyvinyl alcohol, and the like
(11) Bases: soybean oil, beef oil, triolein, phospholipid, dihydrocholesterol, carnauba wax, liquid paraffin, octyldodecyl myristate, dimethylpolysiloxane, and the like
(12) Lubricants: magnesium stearate, carnauba wax, starch, silica, sucrose stearate, calcium silicate, kaolin, gypsum, borax, talc, and the like
(13) Stabilizers: butylhydroxytoluene, butylhydroxyanisole, tocopherol, ascorbic acid, and the like
(14) Preservatives: sodium dihydrogen phosphate and the like
(15) Taste masking agent: saccharin, sucrose, maltose, and the like
(16) Odor masking agents: cocoa powder, mint oil, cinnamon powder, and the like
(17) Emulsifiers: polyoxyethylene (degree of polymerization: 20) sorbitan monooleate (Polysorbate 80), polyoxyethylene nonylphenyl ether, sodium lauryl sulfate, triethyl citrate, tributyl citrate, polyethylene glycol, acetyl triethyl citrate, acetyl tributyl citrate, glycerol monostearate, stearic acid, polyvinylpyrrolidone, polyvinyl alcohol, carboxymethyl cellulose, lecithin, gelatin, hyaluronic acid, and the like
(18) Antioxidants: dibutylhydroxytoluene, butylhydroxyanisole, sorbic acid, sodium sulfite, ascorbic acid, erythorbic acid, L-cysteine hydrochloride, and the like
(19) pH Adjusters: phosphoric acid, sodium monohydrogen phosphate, sodium dihydrogen phosphate, and the like
(20) Flavoring agents: 1-menthol, peppermint, and the like
(21) Colorants: tar dye, fluorescent dye, natural pigment, titanium oxide, aluminum oxide, zinc oxide, magnesium oxide, silicon dioxide, light silicic anhydride, magnesium aluminosilicate, magnesium aluminometasilicate, aluminum silicate, yellow iron oxide, and the like One of the above known additives may be used alone, or two or more of them may be used in combination.

When the raw material for bulk drugs or the pharmaceutical additive of the present invention contains one or more of the above known active ingredients or additives which are used optionally, preferably, such raw materials are uniformly mixed by kneading. A known mixing device can be used. Examples include bexmills, rubber choppers, pharmamills, mincing machines, impact crushers, roll crushers, homogenizers, propeller stirrers, mechanical stirrers, and magnetic stirrers.

Forms of the raw material for bulk drugs or the pharmaceutical additive of the present invention are not limited. Examples include emulsions, organic solvent solutions, and powders. In the case of a powder, examples of the shape include an irregularly crushed shape, a scale shape, a pearl shape, a rice grain shape, and a porous spherical shape. Of these, emulsions and powders are preferred in view of compatibility with the process of producing solid formulations. In the case of a powder, an irregularly crushed shape, a pearl shape, and a porous spherical shape are preferred.

When the raw material for bulk drugs or the pharmaceutical additive of the present invention which contains the polyether composition (A) is mixed with one or more of the above known active ingredients or additives which are used optionally, the weight percentage of the active ingredient (s) is preferably 0.1 to 90 wt %, more preferably 0.5 to 85 wt %, based on the weight of the raw material for bulk drugs or the pharmaceutical additive. The weight percentage of the additive(s) is preferably 0.01 to 70 wt %, more preferably 0.03 to 65 wt %, based on the weight of the raw material for bulk drugs or the pharmaceutical additive.

Examples of the form of the bulk drug or the pharmaceutical product of the present invention include liquids, granules, and powders.

The bulk drug or the pharmaceutical product of the present invention can be produced using the polyether composition (A), one or more of the above known active ingredients, and other optional additives by, for example, any of the following known methods including a coating pan method, a fluidized bed coating method, a rolling coating method, and an extrusion granulation method using a screen.

(1) Coating Pan Method

The polyether composition (A) of the present invention, one or more of the above known active ingredients, and other optional additives are mixed using a coating pan to obtain a bulk drug or a pharmaceutical product in the form of granules or powders. Optionally, the bulk drug or the pharmaceutical product may be then compression-molded to obtain a bulk drug or a pharmaceutical product in the form of pills or tablets.

(2) Fluidized Bed Coating Method

The polyether composition (A) of the present invention, one or more of the above known active ingredients, and other optional additives are fluidized and granulated by an air stream using a flow granulator to obtain a bulk drug or a pharmaceutical product in the form of granules or powders. Optionally, the bulk drug or the pharmaceutical product may be then compression-molded to obtain a bulk drug or a pharmaceutical product in the form of pills or tablets.

(3) Rolling Coating Method

The polyether composition (A) of the present invention, one or more of the above known active ingredients, and other optional additives are fluidized and granulated using a rolling granulator in which a horizontal disk is rotated to roll these components on an upper surface of the disk to obtain a bulk drug or a pharmaceutical product in the form of granules or powders. Optionally, the bulk drug or the pharmaceutical product may be then compression-molded to obtain a bulk drug or a pharmaceutical product in the form of pills or tablets.

(4) Extrusion Granulation Method Using a Screen

The polyether composition (A) of the present invention, one or more of the above known active ingredients, and other optional additives are extruded using an extrusion granulator using a screen to obtain a bulk drug or a pharmaceutical product in the form of granules or powders. Optionally, the bulk drug or the pharmaceutical product may be then compression-molded to obtain a bulk drug or a pharmaceutical product in the form of pills or tablets.

EXAMPLES

The present invention is further described below with reference to examples, but the present invention is not limited to these examples. Hereinafter, the "part(s)" indicates part(s) by weight.

Example 1

Production of Polyether Composition (A) Represented by Formula (1) in which $X^1$ to $X^4$ are Hydrogen Atoms An autoclave was charged with the following materials: polyols as starting materials including pentaerythritol (available from Perstorp; containing 99 wt % compound serving as a raw material of a compound in which m=1 in formula (1)) and 1 wt % compound serving as a raw material of a compound in which m=2 in formula (1)) (2.9 parts), and an adduct of pentaerythritol with 4 moles of ethylene oxide ("PNT-40" available from Nippon Nyukazai Co., Ltd.; containing 100 wt % compound in which m=1 in formula (1)) (1.2 parts); and sodium hydroxide (0.027 parts). The autoclave was purged with argon gas, depressurized, and heated to 95° C.

After dehydration at 0.001 to 0.003 MPa and 95° C. for one hour, the temperature was heated to 130° C., and ethylene oxide (996 parts) as an alkylene oxide was gradually dropped over 18 hours in the temperature range of 125° C. to 135° C. while keeping the inner pressure of the autoclave below 0.2 MPa. After completion of the dropping, the mixture was aged at 145° C. to 155° C. for two hours until the inner pressure of the autoclave was equal to the pressure at the start of the dropping. Thus, a polyether composition (A-1) (1000 parts) was obtained.

No unreacted ethylene oxide was detected from the resulting polyether composition (A-1). The polyether composition (A-1) contained a compound in which m=1 in formula (1) in an amount of 99 wt % (weight percentage based on the weight of the polyether composition (A)), had a unimodal molecular weight distribution as determined by GPC measurement described below, had an Mn of 36000 (an average value of a to d in formula (1) was 225), and had a Mw/Mn of 1.06.

<Conditions for Evaluation by GPC>

Device: HLC-8320GPC available from Tosoh Corporation
Column: TSK gel Super AW available from Tosoh Corporation
Sample solution: 0.25 wt % solution in N,N-dimethylformamide (DMF)
Amount of solution to be injected: 10 μL
Flow rate: 0.6 mL/min
Measurement temperature: 40° C.
Mobile phase: DMF
Detector: refractive index detector
Standard substance: standard polyethylene glycol Examples 2 to 11 and Comparative Examples 1 to 4

Polyether compositions (A-2) to (A-11) and comparative polyether compositions (A'-1) to (A'-4) were produced as in Example 1, except that different polyols as starting materials and different alkylene oxides were used as described in Table 1 in different amounts (parts) according to Table 1.

No unreacted alkylene oxide was detected from the resulting polyether compositions (A-2) to (A-11) and comparative polyether compositions (A'-1) to (A'-4).

Table 1 shows the results of the polyether compositions (A-2) to (A-11) and the comparative polyether compositions (A'-1) to (A'-4) in terms of shape of the molecular weight distribution, Mn, Mw/Mn, the average value of a to d in formula (1), and the amount of a compound in which m=1 in formula (1) (weight percentage based on the weight of the polyether composition (A)).

TABLE 1

| | | | Example | | | | | |
|---|---|---|---|---|---|---|---|---|
| | | | 1 | 2 | 3 | 4 | 5 | 6 |
| Polyether composition (A) | | | (A-1) | (A-2) | (A-3) | (A-4) | (A-5) | (A-6) |
| Raw material | Polyol | Pentaerythritol (containing 99 wt % compound serving as raw | 2.9 | 2.9 | 2.8 | 2.8 | 2.9 | 2.9 |

TABLE 1-continued

| | | | | | | | | |
|---|---|---|---|---|---|---|---|---|
| used (parts) | | material of compound in which m = 1 in formula (1) and 1 wt % compound serving as raw material of compound in which m = 2 in formula (1)) | | | | | | |
| | | Dipentaerythritol (containing 100 wt % compound in which m = 2 in formula (1)) | — | — | 0.19 | 0.43 | — | — |
| | | Adduct of pentaerythritol with 4 moles of ethylene oxide (containing 100 wt % compound in which m = 1 in formula (1)) | 1.2 | 1.2 | 1.2 | 1.2 | 1.2 | 1.2 |
| | | Pentaerythritol (containing 85 wt % compound serving as raw material of compound in which m = 1 in formula (1) and 15 wt % compound serving as raw material of compound in which m = 2 in formula (1)) | | | | | | |
| | Alkylene oxide | Ethylene oxide | 996 | 846 | 235 | 2611 | — | 5200 |
| | | Propylene oxide | — | 197 | — | — | — | — |
| | | Tetrahydrofuran | — | — | — | — | 1630 | — |
| | Sodium hydroxide | | 0.027 | 0.027 | 0.010 | 0.040 | 0.027 | 0.048 |
| Shape of molecular weight distribution of (A) | | | Unimodal | Unimodal | Unimodal | Unimodal | Unimodal | Unimodal |
| Mn of (A) | | | 36000 | 37000 | 8500 | 93000 | 64000 | 190000 |
| Mw/Mn of (A) | | | 1.06 | 1.07 | 1.06 | 1.07 | 1.20 | 1.06 |
| Average value of a to d in formula (1) | | | 225 | 225 | 52 | 550 | 225 | 1176 |
| Amount of compound in which m = 1 in formula (1) (%) | | | 99 | 99 | 95 | 90 | 99 | 99 |

| | | | Example | | | | |
|---|---|---|---|---|---|---|---|
| | | | 7 | 8 | 9 | 10 | 11 |
| Polyether composition (A) | | | (A-7) | (A-8) | (A-9) | (A-10) | (A-11) |
| Raw material used (parts) | Polyol | Pentaerythritol (containing 99 wt % compound serving as raw material of compound in which m = 1 in formula (1) and 1 wt % compound serving as raw material of compound in which m = 2 in formula (1)) | 2.9 | 2.9 | 2.9 | 2.9 | 2.9 |
| | | Dipentaerythritol (containing 100 wt % compound in which m = 2 in formula (1)) | 0.19 | 0.19 | 0.19 | 0.19 | 0.05 |
| | | Adduct of pentaerythritol with 4 moles of ethylene oxide (containing 100 wt % compound in which m = 1 in formula (1)) | 1.2 | 1.2 | 1.2 | 1.2 | 1.2 |
| | | Pentaerythritol (containing 85 wt % compound serving as raw material of compound in which m = 1 in formula (1) and 15 wt % compound serving as raw material of compound in which m = 2 in formula (1)) | | | | | |
| | Alkylene oxide | Ethylene oxide | 996 | 280 | 3000 | 4800 | 996 |
| | | Propylene oxide | — | — | — | — | — |
| | | Tetrahydrofuran | — | — | — | — | — |
| | Sodium hydroxide | | 0.027 | 0.027 | 0.027 | 0.027 | 0.027 |
| Shape of molecular weight distribution of (A) | | | Unimodal | Unimodal | Unimodal | Unimodal | Unimodal |
| Mn of (A) | | | 36000 | 10000 | 110000 | 180000 | 36000 |
| Mw/Mn of (A) | | | 1.06 | 1.06 | 1.06 | 1.06 | 1.06 |
| Average value of a to d in formula (1) | | | 216 | 61 | 649 | 1039 | 223 |
| Amount of compound in which m = 1 in formula (1) (%) | | | 95 | 95 | 95 | 95 | 98 |

| | | | Comparative Example | | | |
|---|---|---|---|---|---|---|
| | | | 1 | 2 | 3 | 4 |
| Polyether composition (A) | | | (A'-1) | (A'-2) | (A'-3) | (A'-4) |
| Raw material used (parts) | Polyol | Pentaerythritol (containing 99 wt % compound serving as raw material of compound in which m = 1 in formula (1) and 1 wt % compound serving as raw material of compound in which m = 2 in formula (1)) | 2.8 | 2.8 | — | 2.8 |
| | | Dipentaerythritol (containing 100 wt % compound in which m = 2 in formula (1)) | — | 0.9 | — | — |
| | | Adduct of pentaerythritol with 4 moles of ethylene oxide (containing 100 wt % compound in which m = 1 in formula (1)) | 1.2 | 1.2 | 0.2 | 1.2 |
| | | Pentaerythritol | — | — | 4.0 | — |

TABLE 1-continued

|  |  | | | | |
|---|---|---:|---:|---:|---:|
|  | (containing 85 wt % compound serving as raw material of compound in which m = 1 in formula (1) and 15 wt % compound serving as raw material of compound in which m = 2 in formula (1)) | | | | |
| Alkylene oxide | Ethylene oxide | 5590 | 1244 | 1244 | 205 |
|  | Propylene oxide | — | — | — | — |
|  | Tetrahydrofuran | — | — | — | — |
| Sodium hydroxide | | 0.054 | 0.027 | 0.027 | 0.027 |
| Shape of molecular weight distribution of (A) | | Unimodal | Bimodal | Unimodal | Unimodal |
| Mn of (A) | | 229000 | 42000 | 42000 | 8000 |
| Mw/Mn of (A) | | 1.06 | 1.30 | 1.12 | 1.06 |
| Average value of a to d in formula (1) | | 1302 | 238 | 242 | 48 |
| Amount of compound in which m = 1 in formula (1) (%) | | 99 | 82 | 88 | 99 |

Comparative Example 1 is an example in which the average values of a to d in formula (1) is more than 1200. Comparative Example 2 is an example in which the shape of the molecular weight distribution is bimodal, the molecular weight distribution (weight average molecular weight/number average molecular weight) is more than 1.2, and the amount of a compound in which m=1 in formula (1) is less than 90 wt %.

Comparative Example 3 is an example in which the amount of a compound in which m=1 in formula (1) is less than 90 wt %, and Comparative Example 4 is an example in which the average values of a to d in formula (1) is less than 50.

Examples 12 to 22 and Comparative Examples 5 to 8

Production of Polyether Composition (A) Represented by Formula (1) in which $X^1$ to $X^4$ are Substituents Represented by Formula (2)

For each of the polyether compositions (A-1) to (A-11) obtained in Examples 1 to 11 and the comparative polyether compositions (A'-1) to (A'-4) obtained in Comparative Examples 1 to 4, the polyether composition (5 parts) and sodium t-butoxide (1 part) were dissolved in toluene (100 parts), and subsequently, sodium chloroacetate (1 part) was dropped to the solution at 25° C. over 10 hours, followed by stirring at 40° C. for 10 hours. Subsequently, a 1 M aqueous solution of hydrochloric acid was added to the mixture for liquid separation so as to collect the organic phase which was washed with a saturated saline solution three times. Toluene was removed by vacuum distillation, followed by recrystallization with isopropanol. Thus, polyether compositions (A-12) to (A-22) and comparative polyether compositions (A'-5) to (A'-8) (5.1 parts, each) were obtained.

<Examples 23 to 33 and Comparative Examples 9 to 12> (Production of Polyether Composition (A) Represented by Formula (1) in which $X^1$ to $X^4$ are Substituents Represented by Formula (3))

For each of the polyether compositions (A-12) to (A-22) obtained in Examples 12 to 22 and (A'-5) to (A'-8) obtained in Comparative Examples 5 to 8, the polyether composition (5 parts), dicyclohexylcarbodiimide (1 part), and N-hydroxysuccinimide (1 part) were dissolved in N,N-dimethylformamide (100 parts), followed by stirring at 40° C. for 10 hours. Subsequently, insolubles were removed by filtration and isopropanol (100 parts) was added, followed by cooling to 5° C. A precipitate was obtained by filtration. Again, isopropanol (100 parts) was added, followed by cooling to 5° C., and a precipitate was obtained by filtration. Thus, polyether compositions (A-23) to (A-33) and comparative polyether composition (A'-9) to (A'-12) (4 parts, each) were obtained.

Table 2 shows the results of the polyether compositions (A-23) to (A-33) and the comparative polyether compositions (A'-9) to (A'-12) in terms of shape of the molecular weight distribution, Mw/Mn, and amount of a compound in which m=1 in formula (1) (weight percentage based on the weight of the polyether composition (A)).

Examples 34 to 44 and Comparative Examples 13 to 16

Modification on Bulk Drugs

For each of the polyether compositions (A-23) to (A-33) obtained in Examples 23 to 33 and the comparative polyether compositions (A'-9) to (A'-12) obtained in Comparative Examples 9 to 12, the polyether composition (5 parts), memantine hydrochloride (available from Tokyo Chemical Industry Co., Ltd.) (3 parts), and triethylamine (2 parts) were dissolved in tetrahydrofuran (100 parts), followed by stirring at 40° C. for 5 hours. After the solvent was removed by distillation, isopropanol (100 parts) was added, followed by cooling to 5° C., and a precipitate was obtained by filtration. Thus, bulk drugs (B-1) to (B-11) and comparative bulk drugs (B'-1) to (B'-4) (4 parts, each) modified by the raw material for bulk drugs of the present invention were obtained.

<Evaluation of Formulation Stability after Modification>

The bulk drugs (B-1) to (B-11) and (B'-1) to (B'-4) obtained above were dissolved at a concentration of 10 wt % in sterilized deionized water. The appearance of each aqueous solution after one-month and three-month storage at 25° C. was visually observed, and evaluated by the following criteria. Table 2 shows the results.

No changes occurred. Excellent
Very small color change occurred. Very good
Small color change occurred. Good
Color change occurred. Average
Color change and slight precipitation occurred. Fair
Color change and precipitation occurred. Poor <Evaluation of Over-Time Stability of Drug Efficacy after Modification>

For each aqueous solution subjected to evaluation of the formulation stability, the amount of memantine produced by hydrolysis was quantitated by ultra-performance liquid chromatography (UPLC) under the following conditions, and the ratio (wt %) of the weight of memantine produced by hydrolysis to the weight of the measured sample was calculated. Table 2 shows the results. A lower ratio means less hydrolysis, indicating better over-time stability of drug efficacy after modification.
<Evaluation Conditions for UPLC>
LC system: ACQUITY UPLC H-Class
Column: ACQUITY UPLC CORTECS C+18, 1.6 μm, 2.1× 50 mm
Column temperature: 45° C.
Flow rate: 0.6 mL/min
Amount of solution to be injected: 1.0 μL
Solvent: methanol/water=1/1
MS detector: ACQUITY QDa detector
Ionization mode: ESI(+)
Single ion recording: 180.2 Da
Sampling rate: 10 points/sec
Capillary voltage: 0.8 kV
Cone voltage: 15 V
Probe temperature: 600° C.
<Evaluation of Solubility in Saline Solution>

Each of the bulk drugs (B-1) to (B-11) and (B'-1) to (B'-4) (1.0 g, each) obtained above was added to a saline solution (10 mL) at 25° C., followed by stirring for 30 minutes for dissolution. Thus, samples for evaluation were prepared.

Using a turbidity meter (product name "WA6000" available from Nippon Denshoku Industries Co., Ltd.), the diffusion transmittance (Td) and the total transmittance (Tt) of each sample for evaluation in a cell (optical path length: 10 mm) at 25° C. were measured, and the haze value (Hz) was calculated from the following formula. Table 2 shows the results.

A lower haze value means less haze, indicating higher solubility in the saline solution.

$$HZ = Td/Tt \times 100$$

Examples 45 to 55 and Comparative Examples 17 to 20

Production of Formulation Using Polyether Composition (A) as Pharmaceutical Additive For each of the polyether compositions (A-1) to (A-11) obtained in Examples 1 to 11 and the comparative polyether compositions (A'-1) to (A'-4) obtained in Comparative Examples 1 to 4, the polyether composition (10 parts) and acetaminophen (available from Tokyo Chemical Industry Co., Ltd.) (1 part) were mixed in the form of powder. Subsequently, the mixture was granulated by extrusion using a 1-mm screen. Thus, pharmaceutical granules (C-1) to (C-11) of the present invention and comparative pharmaceutical granules (C'-1) to (C'-4) (11 parts, each) were obtained.

<Evaluation of Formulation Stability of Granules>

The pharmaceutical granules (C-1) to (C-11) and the comparative pharmaceutical granules (C'-1) to (C'-4) obtained above were left to stand in a constant temperature and humidity chamber maintained at 50% RH and 25° C. or 40° C. The appearance of each granule one-month later and three months later was visually observed, and evaluated by the following criteria. Table 3 shows the results.
No changes occurred. Excellent
Very small color change occurred. Very good
Small color change occurred. Good
Color change occurred. Average
Color change and slight deformation occurred. Fair
Color change and deformation occurred. Poor
<Evaluation of Over-Time Stability of Granules>

For each of the pharmaceutical granules (C-1) to (C-11) of the present invention and the comparative pharmaceutical granules (C'-1) to (C'-4), the dissolution rate was measured immediately after the production and after one-month and three-month storage at 50% RH and 25° C., and evaluated by the following evaluation method. Table 3 shows the results. Preferably, the dissolution rate remains the same since the initial stage of production.
<Evaluation Method of Dissolution Rate>

Using a dissolution test machine (a rotating basket method) of Japanese Pharmacopoeia, the pharmaceutical granules (C or C') (40 mg) for evaluation were introduced into a 0.05 mol/L phosphate buffer (pH 6.8) (500 mL) at 37° C. A rotary basket was rotated at 100 rpm, and the amount of acetaminophen dissolved was quantitated by UV absorbance ("UV-1800" available from Shimadzu Corporation, 244 nm). The time at which 80 wt % of the pharmaceutical granules was dissolved was recorded.
<Evaluation of Solubility in Saline Solution>

The solubility of the pharmaceutical granules (C-1) to (C-11) and (C'-1) to (C'-4) obtained above in a saline solution was evaluated in the same manner as in the evaluation of solubility of the bulk drugs (B-1) to (B-11) and comparative bulk drugs (B'-1) to (B'-4) in a saline solution. Table 3 shows the results.

TABLE 2

| | | (A) as raw material ((A) represented by formula (1) in which $X^1$-$X^4$ are substituents represented by formula (3)) | | | | | | | |
|---|---|---|---|---|---|---|---|---|---|
| | | Shape of molecular weight distribution | Average value of Mw/Mn | a to d in formula (1) | Amount of compound in which m = 1 in formula (1) (%) | Formulation stability | | Over-time stability | | Solubility in saline solution |
| | | | | | | One month later | Three months later | One month later | Three month later | Haze value |
| Example 34 (B-1) | (A-23) | Unimodal | 1.06 | 225 | 99 | Excellent | Excellent | 0.1 wt % | 0.2 wt % | 0.1 |
| Example 35 (B-2) | (A-24) | Unimodal | 1.07 | 225 | 99 | Excellent | Very good | 0.4 wt % | 0.5 wt % | 0.1 |
| Example 36 (B-3) | (A-25) | Unimodal | 1.06 | 52 | 95 | Very good | Good | 0.8 wt % | 1.1 wt % | 0.2 |
| Example 37 (B-4) | (A-26) | Unimodal | 1.07 | 550 | 90 | Average | Fair | 1.3 wt % | 1.8 wt % | 1.0 |
| Example 38 (B-5) | (A-27) | Unimodal | 1.20 | 225 | 99 | Good | Average | 1.1 wt % | 1.3 wt % | 0.1 |

TABLE 2-continued

| | | (A) as raw material ((A) represented by formula (1) in which $X^1$-$X^4$ are substituents represented by formula (3)) | | | | | | | Solubility in saline solution |
|---|---|---|---|---|---|---|---|---|---|
| | | Shape of molecular weight distribution | Average value of Mw/Mn | Average value of a to d in formula (1) | Amount of compound in which m = 1 in formula (1) (%) | Formulation stability | | Over-time stability | | Haze value |
| | | | | | | One month later | Three months later | One month later | Three month later | |
| Example 39 (B-6) | (A-28) | Unimodal | 1.06 | 1176 | 99 | Average | Fair | 1.3 wt % | 1.8 wt % | 0.1 |
| Example 40 (B-7) | (A-29) | Unimodal | 1.06 | 216 | 95 | Very good | Good | 0.9 wt % | 1.1 wt % | 0.2 |
| Example 41 (B-8) | (A-30) | Unimodal | 1.06 | 61 | 95 | Very good | Good | 0.8 wt % | 1.1 wt % | 0.2 |
| Example 42 (B-9) | (A-31) | Unimodal | 1.06 | 649 | 95 | Very good | Good | 0.8 wt % | 1.2 wt % | 0.2 |
| Example 43 (B-10) | (A-32) | Unimodal | 1.06 | 1039 | 95 | Very good | Good | 1.2 wt % | 1.6 wt % | 0.2 |
| Example 44 (B-11) | (A-33) | Unimodal | 1.06 | 223 | 98 | Excellent | Very good | 0.4 wt % | 0.5 wt % | 0.1 |
| Comparative Example 13 (B'-1) | (A'-9) | Unimodal | 1.06 | 1302 | 99 | Poor | Poor | 29 wt % | 45 wt % | 0.2 |
| Comparative Example 14(B'-2) | (A'-10) | Bimodal | 1.30 | 238 | 82 | Poor | Poor | 60 wt % | 80 wt % | 5.0 |
| Comparative Example 15(B'-3) | (A'-11) | Unimodal | 1.12 | 242 | 88 | Poor | Poor | 20 wt % | 35 wt % | 4.8 |
| Comparative Example 16(B'-4) | (A'-12) | Unimodal | 1.06 | 48 | 99 | Poor | Poor | 20 wt % | 43 wt % | 0.2 |

TABLE 3

| | Formulation stability | | Over-time stability | | | Solubility in saline solution Haze value |
|---|---|---|---|---|---|---|
| | One month later | Three months later | Immediately after the production | One month later | Three months later | |
| Example 45 (C-1) | Excellent | Excellent | 20 min | 20 min | 20 min | 0.2 |
| Example 46 (C-2) | Excellent | Very good | 20 min | 19 min | 19 min | 0.2 |
| Example 47 (C-3) | Very good | Good | 20 min | 19 min | 18 min | 0.2 |
| Example 48 (C-4) | Average | Fair | 20 min | 18 min | 17 min | 0.9 |
| Example 49 (C-5) | Good | Average | 20 min | 18 min | 18 min | 0.2 |
| Example 50 (C-6) | Average | Fair | 20 min | 18 min | 17 min | 0.2 |
| Example 51 (C-7) | Very good | Good | 20 min | 19 min | 18 min | 0.2 |
| Example 52 (C-8) | Very good | Good | 20 min | 19 min | 18 min | 0.2 |
| Example 53 (C-9) | Very good | Good | 20 min | 19 min | 18 min | 0.2 |
| Example 54 (C-10) | Very good | Good | 20 min | 18 min | 17 min | 0.3 |
| Example 55 (C-11) | Excellent | Very good | 20 min | 19 min | 19 min | 0.2 |
| Comparative Example 17 (C'-1) | Poor | Poor | 20 min | 45 min | 120 min | 0.2 |
| Comparative Example 18 (C'-2) | Poor | Poor | 20 min | 5 min | 4 min | 7.0 |
| Comparative Example 19 (C'-3) | Poor | Poor | 20 min | 10 min | 8 min | 5.0 |
| Comparative Example 20 (C'-4) | Poor | Poor | 20 min | 35 min | 100 min | 0.4 |

The results in Table 2 and Table 3 show that the raw materials for bulk drugs or the pharmaceutical additives of the present invention have excellent formulation stability and excellent over-time stability of drug efficacy, as compared to the comparative raw materials for bulk drugs or pharmaceutical additives.

If haze occurs when a pharmaceutical product is dissolved in a saline solution, it makes it difficult to determine the dissolution end point of the pharmaceutical product. Thus, particularly when the pharmaceutical product is used as an injection, the haze is preferably as low as possible. Here, when the polyether composition (A) of the present invention contained a compound in which m=1 in formula (1) in an amount of 95 wt % or more based on the weight of the polyether composition (A), the pharmaceutical products containing the polyether composition (A) showed hardly any haze when dissolved in the saline solution. This shows that the polyether composition (A) is particularly excellent as a raw material for bulk drugs or a pharmaceutical additive.

INDUSTRIAL APPLICABILITY

The present invention provides a raw material for bulk drugs or a pharmaceutical additive which provides excellent formulation stability and excellent over-time stability of drug efficacy when used to modify a bulk drug, a polypeptide, a bioactive protein, an enzyme, and the like. In addition, a bulk drug or a pharmaceutical product containing the raw material for bulk drugs or the pharmaceutical additive of the present invention has excellent formulation stability and excellent over-time stability of drug efficacy after modification of a bulk drug, a polypeptide, a bioactive protein, an enzyme, and the like, thus achieving higher quality of pharmaceutical products.

The invention claimed is:
1. A raw material for bulk drugs or a pharmaceutical additive, comprising:
   a polyether composition (A) represented by formula (1), wherein the polyether composition (A) has a unimodal molecular weight distribution,
   the polyether composition (A) has a ratio (Mw/Mn) of the weight average molecular weight (Mw) to the number average molecular weight (Mn) of 1.20 or less, and
   the polyether composition (A) contains a compound in which m is 1 in formula (1) in an amount of 90 wt % or more based on the weight of the polyether composition (A),

[Chem. 1]

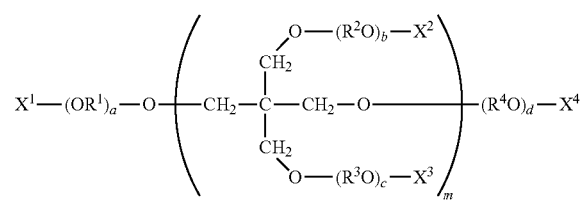

(1)

in formula (1), $OR^1$, $R^2O$, $R^3O$, and $R^4O$ are each independently a C2-C8 oxyalkylene group; when each of these moieties exists in the plural number, each $OR'$, each $R^2O$, each $R^3O$, and each $R^4O$ may be the same as or different from each other; these moieties may be bonded randomly or in block; a, b, c, and d are each independently an integer of 50 to 1200; $X^1$ to $X^4$ are each independently a hydrogen atom, a substituent represented by formula (2), or a substituent represented by formula (3); and m is an integer of 1 to 10,

[Chem. 2]

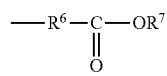

(2)

[Chem. 3]

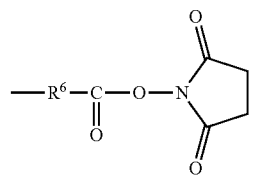

(3)

in formulas (2) and (3), $R^6$ is a C1-C10 alkylene group; in formula (2), $R^7$ is a hydrogen atom or a C1-C15 monovalent hydrocarbon group in which a hydrogen atom may be replaced by a C1-C10 alkoxy group; and when a substituent represented by formula (2) or (3) exists in the plural number in formula (1), each $R^6$ and each $R^7$ in these substituents may be the same as or different from each other.

2. The raw material for bulk drugs or the pharmaceutical additive according to claim 1
   wherein each of $OR^1$, $R^2O$, $R^3O$, and $R^4O$ in formula (1) is an oxyethylene group.

3. The raw material for bulk drugs or the pharmaceutical additive according to claim 1,
   wherein the amount of the polyether composition (A) is 0.1 to 99.5 wt % based on the weight of the raw material for bulk drugs or the pharmaceutical additive.

4. A bulk drug or a pharmaceutical product, comprising:
   the raw material for bulk drugs or the pharmaceutical additive according to claim 1.

5. The raw material for bulk drugs or the pharmaceutical additive according to claim 2,
   wherein the amount of the polyether composition (A) is 0.1 to 99.5 wt % based on the weight of the raw material for bulk drugs or the pharmaceutical additive.

6. A bulk drug or a pharmaceutical product, comprising:
   the raw material for bulk drugs or the pharmaceutical additive according to claim 2.

* * * * *